United States Patent [19]

Shapiro

[11] Patent Number: 5,314,440

[45] Date of Patent: May 24, 1994

[54] MICROSURGICAL SCISSOR APPARATUS

[76] Inventor: Henry Shapiro, 328 Downham Ct., Walnut Creek, Calif. 94598

[21] Appl. No.: 953,075

[22] Filed: Nov. 2, 1992

[51] Int. Cl.$^5$ .............................................. A61B 17/32
[52] U.S. Cl. .................................... 606/174; 606/167; 606/171
[58] Field of Search .................. 128/749, 751; 604/22; 606/1, 45, 46, 137, 138, 148, 167-169, 172, 174, 177, 182, 113, 127

[56] References Cited

U.S. PATENT DOCUMENTS

| | | | |
|---|---|---|---|
| Re. 15,071 | 3/1921 | Ermold | 606/112 |
| 984,756 | 2/1911 | Frisch | 606/174 |
| 2,691,370 | 10/1954 | Wallace | 606/174 |
| 3,752,161 | 8/1973 | Bent | 606/169 |
| 4,848,338 | 7/1989 | Satnick et al. | 606/1 |
| 4,877,026 | 10/1989 | Laforcade | 606/171 |

Primary Examiner—Stephen C. Pellegrino
Assistant Examiner—Glenn Dawson
Attorney, Agent, or Firm—George W. Wasson

[57] ABSTRACT

A microsurgical instrument providing scissor action cutting elements at the end of an elongated tubular housing. The cutting elements are at the free end of a tubular housing that is adapted to be inserted into a surgery site and has one end attached to a motion producing portion of the instrument that is outside the surgery site. The cutting elements are formed at extensions of elongated shaft members one of which reciprocates within the tubular housing. One of the elongated shafts is fixed within the tubular housing near the end attached to the motion producing portion. The elongated shaft members are formed adjacent to the free end of the tubular member to maintain the scissor action cutting elements in firm engagement.

15 Claims, 4 Drawing Sheets

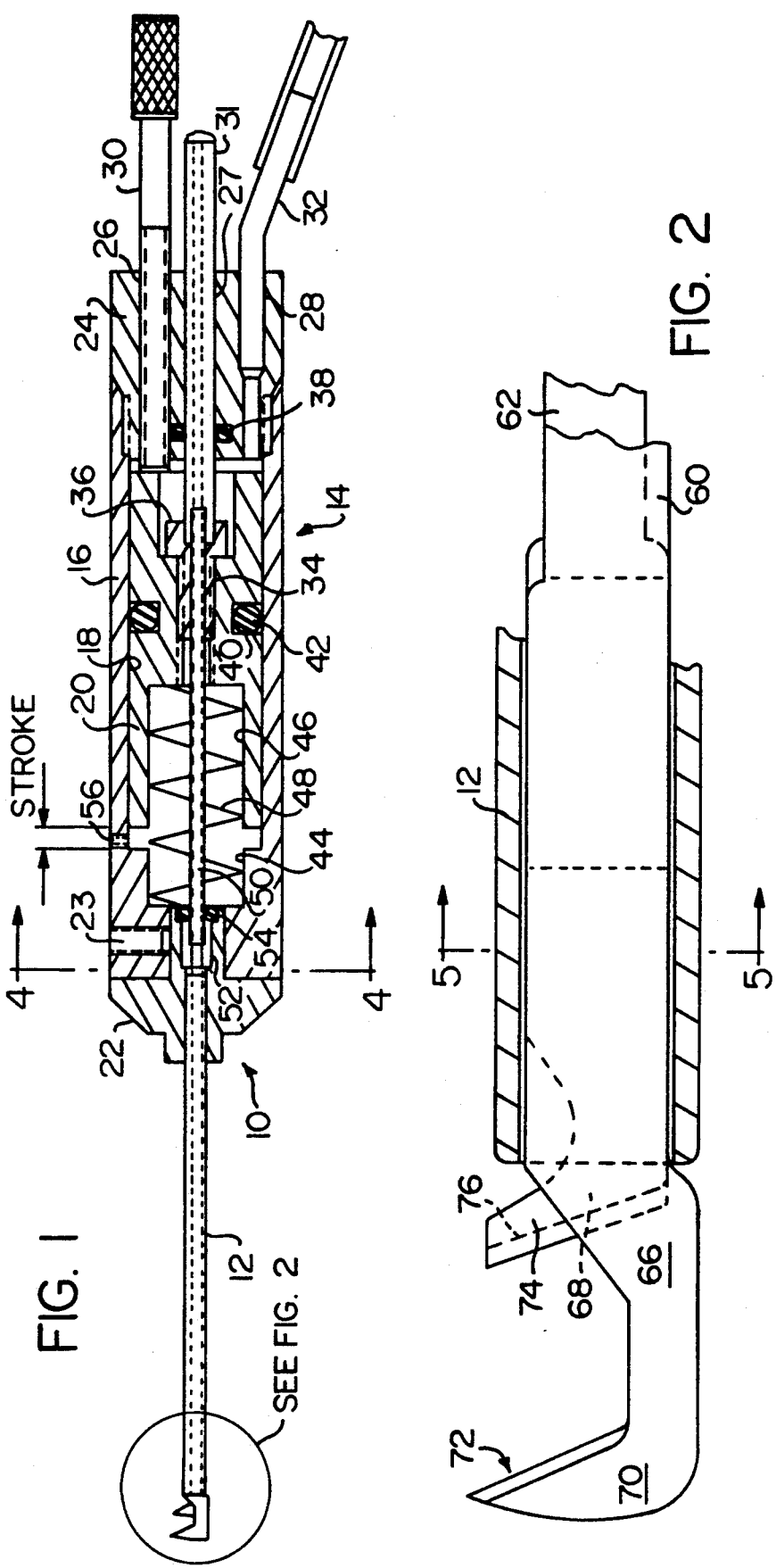

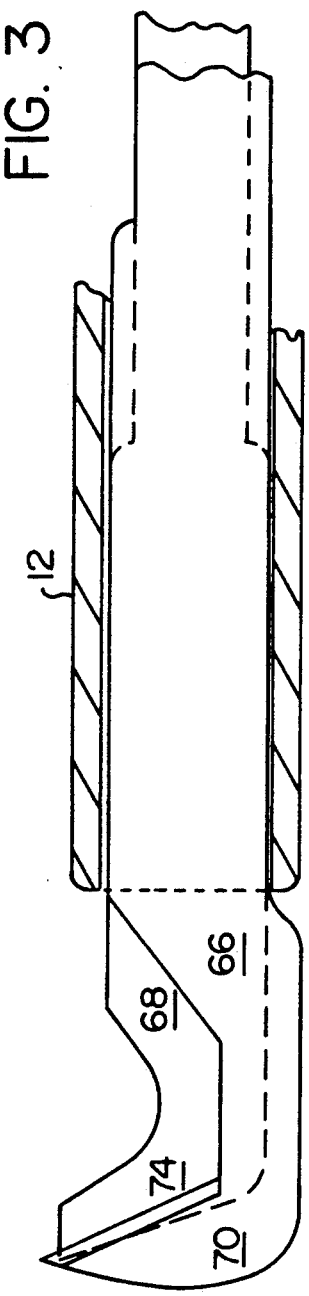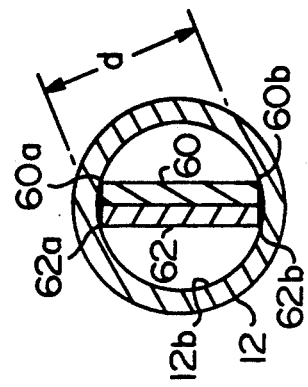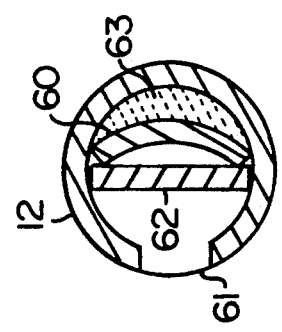

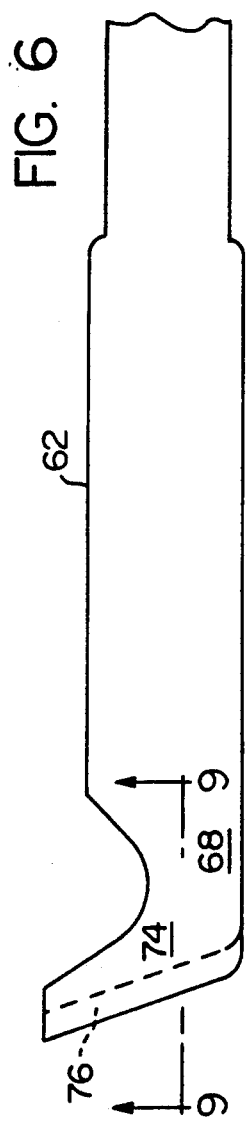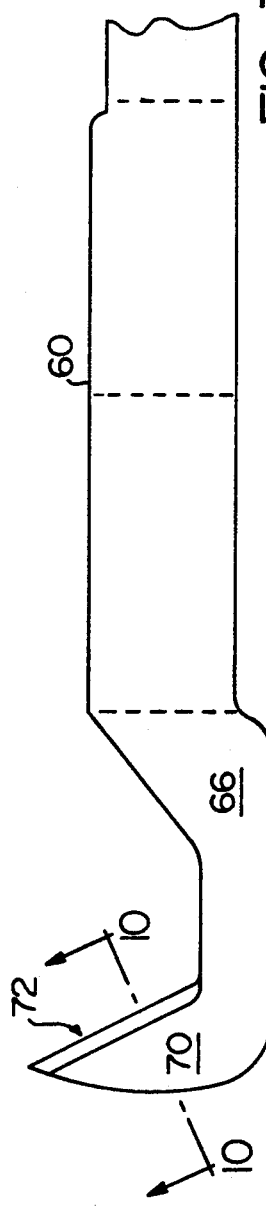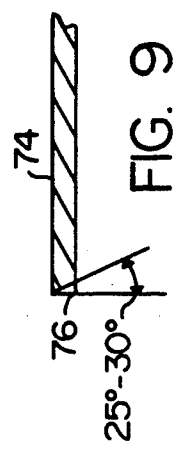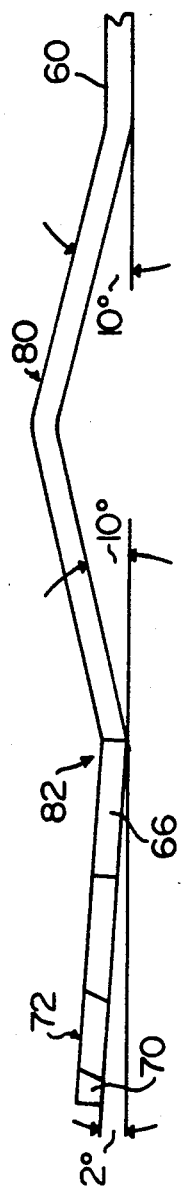

MICROSURGICAL SCISSOR APPARATUS

This invention relates generally to a surgical instrument and more particularly to microsurgical instrument having scissor action cutting surfaces acting at the end of an elongated tubular housing that is adapted to be inserted into the region where surgery is to be performed. One use of the apparatus of the present invention is in performing opthalmic surgery.

BACKGROUND OF THE INVENTION

The use of an elongated tubular instrument for insertion into a surgical site is known and such instruments have been used in performing microsurgical operations within eyes and other internal portions of a patient. In such microsurgical operations it is frequently necessary to cut materials within the surgery site and the need for very small scissor action surgical instruments for performing such cutting have been needed. One such scissor action apparatus is shown in H. de Laforcade U.S. Pat. No. 4,877,026, issued Oct. 31, 1989 for Surgical Apparatus. That patent lists several patents stated to be exemplified of the state of the art for microsurgical instruments.

The elongated tubular members of microsurgical instruments that are inserted into the surgical site are used to transfer motion from motion producing elements outside of the surgical site to elements that are within the surgical site. It becomes necessary for successful useage of the instruments that the moving elements at the end of the elongated tubular member within the surgical site accomplish their movements in a smooth and controlled manner and with a minimum of undesirable or uncontrolled movements. Accomplishing the control of the moving elements and the reduction of motion resistance through the elongated tubular member has been the objective of many developments in the microsurgical instruments.

In scissor action cutting elements functioning at the end of an elongated tubular member where two cutting surfaces are moved with respect to each other it becomes desirable to cause the scissor cutting surfaces to move in a smooth motion and at a substantially uniform cooperating engagement throughout the entire scissor action. Accomplishing those desires at the free end of an elongated tubular microsurgery element becomes difficult.

Accordingly, one object of the present invention is the provision of a microsurgical apparatus having scissor action cutting elements at the free end of an elongated tubular member adapted to be inserted into a surgery site with motion elements outside of the surgery site for transfering motion through the tubular member to cause the scissor action at the cutting elements within the surgery site.

A further object of the present invention in accord with the preceeding object is an assembly of elements and members in a microsurgical instrument that will permit smooth cutting motion at the scissor action cutting elements within a surgical site.

Another object of the present invention in accord with the preceeding objects is a construction and assembly of elements that will cause the scissor action operating elements at the free end of a tubular element to be firmly pressed against each other.

These and other objects and features of the present invention will be readily apparent to those skilled in the art from the appended drawings and specification illustrating a preferred embodiment wherein:

BRIEF DESCRIPTION OF THE DRAWINGS

FIG. 1 is a cross-sectional assembly view of the surgical instrument of the present invention showing the hand held motion producing portion and the elongated tubular portion of the instrument.

FIG. 2 is an enlarged partial sectional view of the circled protion A of FIG. 1 showing the scissor elements in their open position.

FIG. 3 is an enlarged partial sectional view of the circled portion A of FIG. 1 showing the scissor elements in their closed position.

FIG. 4 is a sectional view taken along the lines 4—4 of FIG. 1.

FIG. 5 is a sectional view taken along the lines 5—5 of FIG. 2.

FIG. 6 is an elevational view of the cutting end of the movable cutting element.

FIG. 7 is an elevational view of the cutting end of the stationary cutting element.

FIG. 8 is a top plan view of the stationary cutting element of FIG. 7 showing bends in the stationary element for accomplishing stability within the elongated tubular member.

FIG. 9 is a sectional view taken along the lines 9—9 of FIG. 6.

FIG. 10 is a sectional view taken along the lines 10—10 of FIG. 7.

DESCRIPTION OF THE PREFERRED EMBODIMENT

Figure 11:
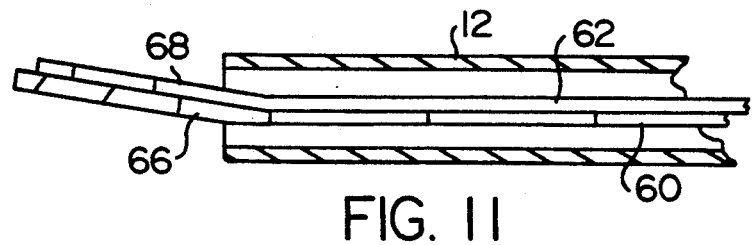
FIG. 11 is a sectional view showing the interaction of the stationary and movable cutting elements at the open end of the tubular member.

Referring to FIG. 1 of the drawings in detail, reference numeral 10 designates the assembled surgical instruments of the present invention with its cutting end in the form of an elongated tubular housing 12 and its stationary or hand held portion 14. The elongated tubular housing 12 has one end attached to the stationary portion 14 and a free end that is intended to be positioned within the surgery site. Within the stationary driving end 14 the reciprocating motion is developed for the cutting portions within and outside the free end of the tubular housing 12. The stationary driving end includes connections for actuating the motion producing elements and for adjusting elements within the assembled surgical instrument.

The driving end 14 could have many differing forms, the form shown here is a preferred embodiment that provides the relative motion within the cutting end 12. The driving end 14 is preferrably cylindrical and includes a body portion 16 having an internal cylindrical cavity 18 for cooperation with a piston 20. One end of the body portion 16 is closed by a needle holder 22 held in the body portion 16 by set screw 23. The needle holder has a central hole through which the elongated tubular housing or needle portion 12 of the probe passes. The other end of the body portion 16 is internally threaded to receive a threaded end of a cover 24. The cover 24 includes passageways 26, 27 and 28 for a stroke adjuster 30, an assembly tube 31 and an air tube 32, respectively.

The piston 20 has a central threaded hole 34 and a hollow adapter 36 is threaded into the hole 34 to provide an internal passageway for the assembly tube 31 whose function will be more fully described later. The assembly tube 31 is secured to the inside of the adapter 36 by means not herein shown and passes through the end cover 24 through an O-ring 38 that functions to seal the tubing 31 for reciprocal movement through the cover 24 with the piston 20. The piston is provided with a circumferential groove 40 for accommodating an O-ring 42 to seal the piston 20 within the cavity 18 and to provide for reciprocating movement of the piston within the cavity. The body portion 16 has a reduced diameter extension 44 of the cavity 18 and the piston 20 has an internal reduced diameter cavity 46 with the two reduced diameter cavities aligned and adapted to accommodate a spring 48. The spring 48 is compressed on movement of the piston 20 within the cavity 18 and biases the piston 20 away from the needle end 12 of the instrument 10. A hollow tubing 50 is secured, by means not herein shown, to the adapter 34 and extends through the cavity 18 within the spring 48 and into a hollow cavity 52 at the inside of the needle holder 22. The outside to the tubing 50 is sealed against the inside of the cavity 52 by an O-ring 54 that permits the tubing 50 to move with the piston 20 and to reciprocate within the cavity 52. A vent hole is provided at 56 adjacent to the end of cavity 18 to provide for relief of pressure as the piston moves within the cavity.

The stroke adjuster knob 30 is threaded through the passageway 26 and functions to limit the return position of the piston 20 within the cavity 18 as the piston is biased by the spring 48. Pressure applied through the air tube 32 causes the piston to move toward the needle holder 22 of the instrument and release of pressure through the tube 32 permits the piston 20 to be returned to its biased position.

The scissor action elements of the present invention are shown in FIGS. 2 and 3 in enlarged partial cross-section of the circled portion A of FIG. 1. The elongated tubular housing 12 is attached to the needle holder 22 so as to be firmly held to the body portion 14 within the holder 22. The tubular housing 12 encloses a pair of elongated shaft members 60 and 62. Shaft member 60 is a stationary member within the tubular housing and is fixed, as by being welded, to the inside of the tubular housing 12 at the inside of the needle holder 22 as shown in FIG. 4. The welded attachment of stationary shaft member 60 is accomplished, as shown in FIG. 4, by pressing a welding instrument against the shaft member 60 in the tubular member and then welding, as at 63, the shaft 60 to the inside of the tubular member 12. It should be understood that the welding shown in FIG. 4 is performed before the movable shaft member 62 is inserted into the tubular member 12. Shaft member 62 is movable within the tubular housing 12 through a connect ion to the piston 20 within the hand held portion 14 of the instrument. As shown in FIG. 5 the two elongated shaft members 60 and 62 are rectangular in cross-section and have outer surfaces that terminate in corners as at 60a, 60b, 62a and 62b, that are dimensionally selected to provide for abutting contact and a sliding relationship with the inner tubular wall 12b of the tubular housing 12. Shaft member 62 is movable within the tubular housing and has a sliding relationship with the fixed elongated shaft 60 along the housing. The inside of the tubular housing is lapped to a very smooth, almost mirror-like finish to assure that the sliding action of the movable shaft is unimpeded within the interior of the tubular housing.

Considering now the assembly of the movable shaft member 62 to the surgical instrument assembly, the movable shaft member 62 is inserted into the assembly from the open end of the tubular housing 12 after the housing and needle holder 22 assembly has been attached to the hand held portion 14. The assembly of the tubular member 12 and needle holder 22 includes the stationary shaft member 62 welded to the inside of the tubular member and the tubular member secured to the needle holder. The movable shaft member 60 constitutes a long shaft member that is long enough to extend from the cutting end of the tubular shaft through the hand held portion 14 and through the assembly tube 31 to the exterior of the assembled surgical instrument. When so inserted, the cutting end of the movable shaft 60 is aligned with the cutting end of the stationary shaft 62 at a desired cutting alignment with the piston 20 at its forward position (with spring 48 compressed). When so aligned, the end of the movable shaft member 60 within the assembly tube 31 is fixed to the inside of that tubing, by means such as soldering, and the end of the tubing is sealed. The movable shaft member is thus operationally fixed to the piston 20 for reciprocatory movement with the piston as it reciprocates within the cavity 18. Within the hand held portion, the movable shaft 62 is fixed to the tubing 31, passes through the adapter 34 with that tubing, then is enclosed within tubing 50 at the center of the spring 48, then passes with tubing 50 into the needle holder 22 at the hollow cavity 52, and into the tubular housing 12 in sliding alignment with the stationary shaft 60 and the inside of the tubular member 12.

FIGS. 2 & 3 illustrate enlargements of the circled portion A of FIG. 1 and show the cutting surfaces of the scissor action portion of the present invention. The scissor action portion includes the cooperation of an extension 66 of the fixed elongated shaft 60 and an extension 68 of the movable elongated shaft 62 beyond the open end of the tubular housing 12.

Considering first the fixed elongated shaft 60 and its cutting surface, FIG. 7 illustrates that member alone where the extension 66 is shown formed with a hook shaped contour terminating in a cutting blade at 70 with a cutting edge at 72. The cutting blade 70 is formed at a transverse angle to the longitudinal axis of the shaft 60; that angle being about 25°. FIG. 10 shows a cross-section through the cutting edge 72 of cutting blade 72 along the lines 10—10 of FIG. 7 illustrating the cutting edge 72 formed at an angle of between 30° and 40° to the plane of the shaft 60. The sharpened cutting edge has its edge directed toward the free or open end of the tubular housing 12.

The movable elongated shaft member 62 and its cutting surface is illustrated in FIG. 6 where the extension 68 is shown formed with a hook shaped contour terminating in a chisel shaped cutting blade 74 with a cutting edge at 76. The cutting blade 74 is formed at a transverse angle to the longitudinal axis of the shaft 62; that angle being about 35° FIG. 9 shows a cross-section through the cutting edge 76 of cutting blade 74 along the lines 9—9 of FIG. 6 illustrating the cutting edge 76 formed at an angle of between 25° and 30° to the plane of the shaft 62. The sharpened cutting edge has its edge directed toward the cutting edge 72 of the fixed elongated shaft member 60.

The effect of the different transverse angles of the cutting blades 70 and 74 can be seen in FIG. 3 where the blades are shown in their full stroke position. It should be apparent that the base of the cutting blade 74 contacts the base of the cutting blade 70 as the movable shaft begins its move toward the end of the fixed shaft. As that axial movement continues, the cutting edges 72 and 76 continue their contact until the completion of the stroke of the movable member 62 places the end of the cutting edges in the postion as shown in FIG. 3. The difference in the transverse angles cutting blades is responsible for the improved cutting action of the cutting edges.

FIG. 8 illustrates the bending of the fixed elongated shaft member 60 at the end near the extension 66 for the purpose of accomplishing stability of the cutting end of the surgical instrument. Stability and smoothness of motion of the cutting surfaces of the scissor action elements are important to the usefulness of the surgical instrument. The fixed and movable elongated shaft members are maintained in alignment by the sliding contact of the movable member with the inside of the tubular housing and with the fixed elongated shaft. That sliding contact would permit slight movements between the cutting surfaces at the extensions of the elongated shafts if the shafts were not held in reasonable firm contact with the tubular housing at the open end of the housing. To accomplish a stable and firm control over the elongated shafts, the fixed shaft member 60 is formed with an offset portion at 80. The offset portion is offset from the longitudinal axis of the elongated member 60 and toward the position of the movable elongated member when the fixed member is within the tubular housing 12. As shown in FIG. 8, the offset is at about 10° away from and back to the longitudinal axis of the member 60. It should be understood that when the fixed member and the movable members are enclosed within the tubular housing, the offset 80 substantially disappears because the fixed and movable members have only marginal clearances along the inner wall of the tubular housing; the offset bend 80 of the fixed member 60 does bias the fixed member against the movable member and forces the movable member into a firm engagement with the inside wall of the tubular housing. When so firmly held, the movable member 62 is firmly held against lateral movement within the tubular housing.

In addition to the offset bend 80, the fixed elongated shaft member 60 has a transverse bend at 82 in the vacinity of the extension 66 to bend the cutting blade 70 away from the longitudinal axis of the member 60 and effectively toward the central axis of the tubular housing 12 when the fixed member is assembled into the tubular housing. The transverse bend here is illustrated as a bend of about 2°. The effect of this transverse bend 82 on the assembled scissor cutting portion of the surgical instrument is to place the cutting edge 72 of the fixed elongated member 60 slightly across the central axis of the tubular housing 12 in a position to cause the cutting edge 76 to maintain a firm scissor contact with cutting edge 72 as the movable elongated member 62 is reciprocated within the tubular housing 12.

Figure 12:
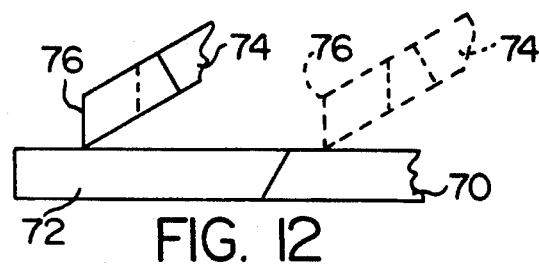
FIG. 12 is an exaggerated represention of the contact between the cutting blades of the scissor action elements.

The effect of the transverse bend 82 is illustrated in the cross-sectional view FIG. 11 where the fixed member bend at the extension 66 causes the extension of the movable member 62 to become slightly offset while maintaining a firm scissor contact between the cutting edges of the members. An exaggerated representation of that firm scissor contact is shown in FIG. 12 where the contact of the cutting edges is shown in the open position of the movable member 62 in phantom and in the close position in solid lines.

Figure 13:
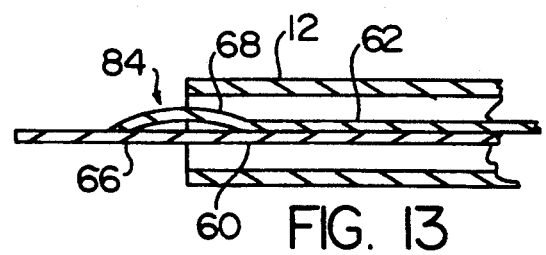
FIG. 13 is a sectional view through an alternative form of bending for the scissor action elements.
Figure 14:
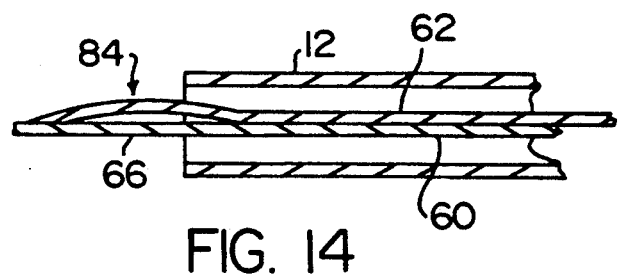
FIG. 14 is a section view showing the contact of the cutting blades of FIG. 13 at the open end of the tubular member.

An alternative formation of the elongated shaft members 60 and 62 is shown in FIGS. 13 and 14. In this alternative form, the movable elongated shaft member 62 is formed with an arcuate bend at 84 in a direction transverse to the longitudinal axis of the member 62. The arcuate bend 84 biases the movable member 62 toward the fixed member 60 to cause the desired firm scissor contact between the cutting edge 76 of the movable member 62 with the cutting edge 72 of the fixed member 60. As illustrated in FIG. 13, the arcuate bend 84 is reduced in transvers direction within the tubular housing 12 because of the constraint of the inner wall of the tubular housing but expands to somewhat the form shown in FIG. 14 as the movable member 62 exits from the tubular housing 12.

The foregoing is a description of the elements that are assembled to form the microsurgical instrument of the present invention. The elements of this instrument have dimensions of about the following sizes. The entire instrument is about 3 inches long with the tubular housing and cutting edge extensions extending about 1.187 inches beyond the needle holder and the body portion being about 1.750 inches. The body portion is about 0.375 inches in diameter and the tubular housing is about 0.050 in outside diameter and about 0.036 in inside diameter. The fixed and movable elongated shaft members are about 0.025 inches in transverse height and about 0.0035 inches in transverse width. The stroke of the piston 20 and therefore the movement of the cutting surface of the movable member 62 is about 0.040 inches maximum and reducable by adjustment of the adjustable stroke adjuster 30. The body member 16 may be made of aluminum and the tubular housing 12 is preferrably made of 304 stainless steel. The stationary and movable blades are preferrably made of 420 stainless steel. The cuttings elements of the present invention are assembled and hardened to produce smooth, hard cutting surfaces at the cutting edges and spring like forming at the transverse bends.

The assembled apparatus of the foregoing description constitutes a scissor action cutting attachment for a surgical instrument or the assembled instrument having an elongated tubular housing enclosing a fixed and a movable shaft element. The shaft elements include extensions that extend beyond the open end of the tubular housing and those extensions are formed into sharpened cutting blades that cooperate in a scissor action as one of the shaft elements is reciprocated with respect to the other within the tubular housing. In a preferred form the shaft elements include a fixed element and a movable element with the fixed element being fixed at one end of the tubular member and formed at the open end of the tubular member in a manner to establish a firm contact with the movable shaft element and the inside of the tubular housing. The shaft elements are further formed at the open end of the tubular housing to provide for an improved scissor cutting action between the cutting edges of the elements. The construction and formation of the shaft elements and their contact with the tubular member are designed to provide a smooth, vibration free action at the scissor action cutting surfaces of the instrument.

While certain preferred embodiments of the present invention have been specifically disclosed and described, it should be understood that the invention is not limited thereto, as many variations will be readily apparent to those skilled in the art and the invention is to be given its broadest possible interpertation within the terms of the following claims.

I claim:

1. A scissor action cutting attachment for a surgical instrument, said surgical instrument having a motion producing portion with a movable part and a non-movable part, said attachment being adapted for performing microsurgical procedures, said attachment comprising,
   a) an elongated rigid tubular housing, said tubular housing having one end adapted to be attached to said non-movable part of said motion producing portion of said surgical instrument and a free end adapted to support and position a portion of said scissor action cutting attachment in a surgical site, said tubular housing having a circular cross section and having an inner tubular wall,
   b) a fixed elongated shaft member positioned within said tubular housing and attached to said inner tubular wall of said tubular housing,
   c) a movable elongated shaft member positioned within said tubular housing in sliding relationship with said fixed elongated shaft member and with said inner tubular wall of said tubular housing, said movable elongated shaft member adapted to be attached to said movable part of said motion producing portion in a manner to be reciprocally axially movable within said tubular housing and with respect to said fixed elongated shaft member,
   d) said fixed and movable elongated shaft members including portions thereof extending beyond said free end of said tubular housing and establishing cooperating surfaces exterior of said tubular housing,
   e) a transverse sharpened cutting blade formed in said extending portion of said fixed elongated shaft member including a cutting edge at a transverse angle to a plane perpendicular to the longitudinal axis of said tubular housing and directed toward said free end of said tubular housing,
   f) a transverse sharpened cutting blade formed in said extending portion of said movable elongated shaft member including a cutting edge at a transverse angle to a plane perpendicular to the longitudinal axis of said tubular housing and directed toward said cutting edge of said fixed elongated shaft member,
   g) whereby reciprocal axial movement of said movable elongated shaft member within said tubular housing causes said cutting edges of said elongated shaft members to effect an axial scissor action exteriorly of said tubular housing;
   e) and said cutting blades of said fixed and movable elongated shaft members exterior of said free end of said tubular housing having a relative tension bias toward each other so as to cause said cutting blades to maintain firm scissor contact with each other as said movable elongated shaft member is reciprocated axially.

2. The scissor action cutting attachment of claim 1 wherein a surface of said extending portion of both said fixed and movable elongated shaft members contact each other adjacent to said cutting blades, and said cutting blade of said fixed elongated shaft member is formed at a transverse angle across said extending portion of said fixed elongated shaft member from a start portion where said blade is formed in said extending portion of said fixed elongated shaft member to an end of said cutting blade, and said cutting blade of said movable elongated shaft member is formed at a transverse angle across said extending portion of said movable elongated shaft member from a start portion where said blade is formed in said extending portion of the moveable elongated shaft member to an end of said cutting blade, said transverse angles of said cutting blades being different such that, when said movable elongated shaft member is reciprocated within said tubular housing, said cutting blades first contact with each other at said start portions of said transverse angles and proceed to the ends of each cutting blade.

3. The scissor action cutting attachment of claim 1 wherein said fixed elongated shaft member adjacent to said free end of said tubular housing and within said tubular housing includes an offset portion axially along its length, said offset portion being offset from a longitudinal axis of said fixed elongated shaft member and toward said movable elongated shaft member whereby said offset portion biases said fixed elongated shaft member toward said movable elongated shaft member and biases said movable elongated shaft member against said inner tubular wall of said tubular housing adjacent to said free end of said tubular housing, whereby said fixed and movable elongated shaft members are firmly held against lateral movement of within said tubular housing adjacent to said free end of said tubular housing.

4. The scissor action cutting attachment of claim 1 wherein said cooperating surface of said fixed elongated shaft member at said exterior of said free end of said tubular housing includes a transverse bend from a longitudinal axis of said fixed elongated shaft member with respect to and toward a central axis of said tubular housing so as to bend said cutting blade of said fixed elongated shaft member toward said central axis to maintain said cooperating surface of said fixed elongated shaft member in firm scissor contact with said cooperating surface of said movable elongated shaft member as said movable elongated shaft member is reciprocated.

5. A surgical instrument for performing microsurgical procedures and including a motion producing portion and an elongated rigid tubular housing, said tubular housing having one end attached to said motion producing portion and a free end for insertion into a surgical site for performing said microsurgical procedures, said tubular housing having a longitudinal axis and a circular cross section and having an inner tubular wall supporting therein a fixed and a movable elongated shaft member, each of said shaft members having a longitudinal axis substantially parallel to said longitudinal axis of said tubular housing, said motion producing portion including means for producing relative axial motion between said fixed and movable elongated shaft members within said tubular housing, said fixed and movable elongated shaft members terminating in cooperating surfaces including sharpened blades having cutting edges exterior of said free end of said tubular housing, said cutting edges being functional to perform said microsurgical procedures, the improvements comprising:

a) said fixed and movable elongated shaft members having outer surfaces terminating in corners, said corners abutting said inner tubular wall of said tubular housing, said shaft members being held in a spacial relationship relative to each other and said inner tubular wall by said corners, whereby said shaft members occupy only a portion of the space in said tubular housing, said movable elongated shaft member being maintained in a sliding relationship within said fixed shaft member and said inner tubular wall;

b) said fixed elongated shaft member being attached to said inner tubular wall of said tubular housing adjacent to the attachment of said tubular housing and said motion producing portion;

c) said movable elongated shaft member being operably connected to a portion of said motion producing portion whereby said movable elongated shaft member is reciprocated axially relative to said fixed elongated shaft member;

d) said sharpened blade and said cutting edge of said fixed elongated shaft member directed along a plane transverse to the longitudinal axis of said tubular housing, said sharpened blade and said cutting edge of said movable elongated shaft member directed toward said cutting edge of said fixed elongated shaft member, whereby said axial movement of said movable elongated shaft member causes said cutting edges of said elongated shaft members to effect an axial scissor action exteriorly of said tubular housing;

e) and said cooperating surfaces of said fixed and movable elongated shaft members exterior of said free end of said tubular housing having a relative tension bias toward each other so as to cause said cooperating surfaces to maintain said cutting edges in firm scissor contact with each other as said movable elongated shaft member is moved axially.

6. The surgical instrument of claim 5 wherein said fixed elongated shaft member adjacent to said free end of said tubular housing and within said tubular housing includes an offset portion axially along its length, said offset portion being offset from said longitudinal axis of said fixed elongated shaft member and toward said movable elongated shaft member whereby said offset portion biases said fixed elongated shaft member toward said movable elongated shaft member and biases said fixed elongated shaft member against said inner tubular wall of said tubular housing adjacent to said free end of said tubular housing, whereby said fixed and movable elongated shaft members are firmly held against lateral movement within said tubular housing adjacent to said free end of said tubular housing.

7. The surgical instrument of claim 5 wherein said fixed elongated shaft member at said cooperating surface exterior of said free end of said tubular housing includes a transverse bend from said longitudinal axis of said fixed elongated shaft member with respect to and toward a central axis of said tubular housing so as to bend said blade of said fixed elongated shaft member toward said central axis to maintain firm scissor contact with said blade of said movable elongated shaft member as said movable elongated shaft member is reciprocated.

8. The surgical instrument of claim 5 wherein said motion producing portion includes a body portion adapted to be hand held, an inner cavity within said body portion, a piston adapted to reciprocate a stroke distance within said inner cavity, means for attaching a portion of said movable elongated shaft member to said piston, spring means for biasing said movable elongated shaft member and said piston away from said free end of said tubular housing, and means for moving said piston within said cavity to compress said spring means and move said movable elongated shaft member with respect to said fixed elongated shaft member and within said tubular housing to establish a scissor cutting action having an axial stroke distance at said cooperating surfaces at said free end of said tubular housing.

9. The surgical instrument of claim 8, further comprising an adjustable means attached to said body portion and extending into said inner cavity in a position to contact said piston, said adjustable means being operable to control said axial stroke distance of said piston within said inner cavity whereby said axial stroke distance of said scissor cutting action is controlled at said free end of said tubular housing.

10. The surgical instrument of claim 8, further comprising an air tube passing through said body portion and into said inner cavity, whereby pulses of air through said air tube cause said piston to be moved within said cavity and to thus move said movable elongated shaft member within said tubular housing.

11. The surgical instrument of claim 8 further comprising means contacting said piston within said cavity and extending through said body portion, said movable elongated shaft member being attached to said means contacting said piston to permit manual movement of said piston within said cavity to thus move said movable elongated shaft member within said tubular housing.

12. The surgical instrument of claim 5 wherein said motion producing portion for producing relative axial motion between said fixed and movable elongated shaft members includes a body portion adapted to be hand held, an inner cavity within said body portion, a piston adapted to reciprocate within said cavity, means for attaching a portion of said movable elongated shaft member to said piston, spring means for biasing said movable elongated shaft member and said piston away from said free end of said tubular housing, and means for moving said piston within said cavity to compress said spring means and move said movable elongated shaft member with respect to said fixed elongated shaft member and within said tubular housing to establish a scissor cutting action at said free end of said tubular housing.

13. The surgical instrument of claim 12 further comprising an adjustable means attached to said body portion and extending into said inner cavity in a position to contact said piston, said adjustable means being operable to control a stroke distance of said piston within said inner cavity.

14. The surgical instrument of claim 12 further comprising an air tube passing through said body portion and into said inner cavity, whereby pulses of air through said air tube cause said piston to be moved within said cavity and to thus move said movable elongated shaft member within said tubular housing.

15. The surgical instrument of claim 12 further comprising means contacting said piston within said cavity and extending through said body portion, said movable elongated shaft member being attached to said means contacting said piston to permit manual movement of said piston within said cavity to thus move said movable elongated shaft member within said tubular housing.

* * * * *